(12) United States Patent
Morrison

(10) Patent No.: US 11,421,267 B2
(45) Date of Patent: Aug. 23, 2022

(54) NUCLEIC ACID AMPLIFICATION AND USE THEREOF

(71) Applicant: Accugenomics, Inc., Wilmington, NC (US)

(72) Inventor: Tom B. Morrison, Wilmington, NC (US)

(73) Assignee: Accugenomics, Inc., Wilmington, NC (US)

( * ) Notice: Subject to any disclaimer, the term of this patent is extended or adjusted under 35 U.S.C. 154(b) by 0 days.

(21) Appl. No.: 16/134,538

(22) Filed: Sep. 18, 2018

(65) Prior Publication Data

US 2019/0256901 A1    Aug. 22, 2019

Related U.S. Application Data

(63) Continuation of application No. 15/226,802, filed on Aug. 2, 2016, now abandoned, which is a continuation of application No. 14/553,679, filed as application No. PCT/US2013/042666 on May 24, 2013, now abandoned.

(60) Provisional application No. 61/651,824, filed on May 25, 2012.

(51) Int. Cl.
| | |
|---|---|
| *C12Q 1/6851* | (2018.01) |
| *C12Q 1/6886* | (2018.01) |
| *C12Q 1/689* | (2018.01) |
| *C12Q 1/70* | (2006.01) |

(52) U.S. Cl.
CPC .......... *C12Q 1/6851* (2013.01); *C12Q 1/689* (2013.01); *C12Q 1/6886* (2013.01); *C12Q 1/701* (2013.01); *C12Q 2600/158* (2013.01); *Y02A 50/30* (2018.01)

(58) Field of Classification Search
CPC ........ C12Q 2527/107; C12Q 2545/107; C12Q 1/6851; C12Q 2561/113; C12Q 1/6886; C12Q 1/689; C12Q 2600/158
See application file for complete search history.

(56) References Cited

U.S. PATENT DOCUMENTS

| | | | |
|---|---|---|---|
| 7,378,241 B2 | 5/2008 | Sagner et al. | |
| 2010/0273173 A1 | 10/2010 | Hirai et al. | |
| 2012/0258524 A1* | 10/2012 | Wittwer | C12Q 1/6818 435/287.2 |

FOREIGN PATENT DOCUMENTS

| | | | |
|---|---|---|---|
| EP | 1072679 A2 | 1/2001 | |
| EP | 1138784 A2 | 10/2001 | |

OTHER PUBLICATIONS

Lyon et al., Quantification of HER2/neu Gene Amplification by Competitive PCR Using Fluorescent Melting Curve Analysis Clinical Chemistry, vol. 47, No. 5, pp. 844-851. (Year: 2001).*
Yeh et al., "Quantification and genotyping of hepatitis B virus in a single reaction by real-time PCR and melting curve analysis," Journal of Hepatology, vol. 41, pp. 659-666. (Year: 2004).*
International Search Report of PCT/US2013/042666, dated Aug. 21, 2013.
Franke-Whittle et al; "Design and application of an oligonucleotide microarray for the investigation of compost microbial communities"; Journal of Microbiological Methods, vol. 62, No. 1, pp. 37-56 (2005).
Offiice Action in corresponding European Patent Application No. 13793331.3 dated Mar. 21, 2017.
Lyon E et al, "Quantification of HER2/neu gene amplification by competitive PCR using fluorescent melting curve analysis", Clinical Chemistry, American Association for Clinical Chemistry, Washington, DC, (May 1, 2001), vol. 47, No. 5, ISSN 0009-9147, pp. 844-851.
Heid C A et al, "Real Time Quantitative PCR", Genome Research, Cold Spring Harbor Laboratory Press, (Oct. 1, 1996), vol. 6, No. 10, ISSN 1088-9051, pp. 986-994.
"Lightcycler operator's manual, version 3.5:Prologue", Lightcycler Operator's Manual, XX, XX, (Oct. 1, 2000), pp. 8-189,1.
Lorena Zentilin et al, "Competitive PCR for precise nucleic acid quantification", Nature Protocols, GB, (Aug. 1, 2007), vol. 2, No. 9, doi:10.1038/nprot.2007.299, ISSN 1754-2189, pp. 2092-2104.

* cited by examiner

*Primary Examiner* — Young J Kim
(74) *Attorney, Agent, or Firm* — Locke Lord LLP; Nicholas J. Di Ceglie, Jr.

(57) ABSTRACT

The invention features compositions and methods that are useful for the measurement of the quantity of a nucleic acid target in a sample.

15 Claims, 6 Drawing Sheets

Specification includes a Sequence Listing.

NUCLEIC ACID AMPLIFICATION AND USE THEREOF

CROSS REFERENCE TO RELATED APPLICATIONS

This application is a continuation of application Ser. No. 15/226,802 filed on Aug. 2, 2016, which application is U.S. patent application Ser. No. 14/553,679 filed on Nov. 25, 2014, which is the national phase under 35 U.S.C. § 371 of PCT International Application No. PCT/US2013/042666, filed on May 24, 2013 which claims the benefit of U.S. Provisional Patent Application Ser. No. 61/651,824, filed May 25, 2012. The entire contents of each application are hereby incorporated by reference herein.

SEQUENCE LISTING

The instant application contains a Sequence Listing which has been submitted electronically in ASCII format and is hereby incorporated by reference in its entirety. Said ASCII copy, created on Jun. 2, 2021, is named 1481795_101US32_SL.txt and is 1,333 bytes in size.

BACKGROUND OF THE INVENTION

Quantitative PCR (qPCR) has excellent lower detection threshold, signal-to-analyte response, and dynamic range. However, most commercially available realtime qPCR platforms are limited in their suitability for diagnostics due to instrument-to-instrument variability, and insufficient quality control (including lack of control for PCR inhibitors). Most methods rely on replicate measurements to provide some control for false negative and positive results; however, this approach requires additional sample consumption and does not control for sample-specific interfering substances such as assay specific inhibitors. This problem is exacerbated by the fact that RNA yield is often low from clinical samples, and this low RNA yield limits the number of assays per test. Furthermore, more tests consume expensive reagents and entail complicated workflows, requiring highly skilled labor and expensive reagents, making the test expensive and possibly slowing widespread adoption and deployment, despite its intrinsic clinical value.

Molecular diagnostics and pharmaceutical companies, clinicians and FDA are struggling with how to deploy qPCR based diagnostics. Commercially available platforms for measuring gene expression, qPCR methods using an internal standard, do not have the inter-site concordance required for accurate outcome scores calculation. The most significant barriers to diagnostic implementation is accurate and robust gene transcript quantification. A clear benefit to improving human health care capabilities would be a system that provides the analytic sensitivity and linear dynamic range of qPCR, while minimizing inter-laboratory analytical variation, cost and sample consumption. Thus, there is an urgent need for diagnostic methods based on the detection of nucleic acid targets in a sample that are clinically deployable and have increased analytic sensitivity, simplified workflow, and improved quality control measures.

SUMMARY OF THE INVENTION

As described below, the present invention features compositions and methods that provide for quantitative PCR that reduces the effect of the hybridization probe on amplification and enhances detection of a nucleic acid target in a sample, such as a biologic sample.

In one aspect, the invention provides a method of amplifying a target nucleic acid molecule in the presence of a detectable nucleic acid probe and a reference nucleic acid molecule, the method involving amplifying the target nucleic acid molecule and the reference nucleic acid molecule in the presence of the detectable nucleic acid probe that is capable of hybridizing to the target nucleic acid molecule and the reference nucleic acid molecule, where the reference nucleic acid molecule is selected as having reduced or no secondary structure in the probe binding site.

In another aspect, the invention provides a method for detecting a target nucleic acid molecule in a sample, the method involving the steps of amplifying the target nucleic acid molecule in the presence of a reference nucleic acid molecule and a detectable nucleic acid probe that is capable of hybridizing to the target nucleic acid molecule and the reference nucleic acid molecule; identifying binding of the detectable nucleic acid probe to the target nucleic acid molecule and determining the melting temperature of the detectable nucleic acid probe to the target nucleic acid molecule; identifying binding of the detectable nucleic acid probe to the reference nucleic acid molecule and determining the melting temperature of the detectable nucleic acid probe to the reference nucleic acid molecule; reducing a difference in yield signal between the melting curves for the target nucleic acid molecule and the reference nucleic acid molecule; and determining the quantity of the target nucleic acid molecule in the sample using the half maximal effective concentration of the reference nucleic acid molecule.

In various embodiments of any of the aspects delineated herein, reducing a difference in the yield signal involves one or more of selecting probe binding sites of the target nucleic acid molecule and the reference nucleic acid molecule that have no differences in secondary structure; selecting the reference nucleic acid molecule as having reduced or no secondary structure in the probe binding site; and scaling the yield signal between the melting curves. In various embodiments of any of the aspects delineated herein, scaling the yield signal between the melting curves involves using a curve fitting algorithm (e.g., a logistic curve fit).

In various embodiments of any of the aspects delineated herein, the probe binding site of the target nucleic acid molecule is selected as having reduced or no secondary structure (e.g., stem-loop structure or pseudoknot structure). In various embodiments of any of the aspects delineated herein, the probe binding site of the target nucleic molecule and the probe binding site of the reference nucleic acid molecule have no differences in secondary structure. In various embodiments of any of the aspects delineated herein, the secondary structure is present at the melting temperature of the nucleic acid molecule. In various embodiments of any of the aspects delineated herein, secondary structure is reduced in one or more primer binding sites of one or more of the target nucleic acid molecule and the reference nucleic acid molecule. In various embodiments of any of the aspects delineated herein, the probe binding site of the target nucleic molecule and the probe binding site of the reference nucleic acid molecule have substantial sequence identity (at least 90, 91, 92, 93, 94, 95, 96, 97, 98, or 99%).

In various embodiments of any of the aspects delineated herein, the target nucleic acid is RNA or DNA. In various embodiments of any of the aspects delineated herein, amplifying is by polymerase chain reaction (PCR), competitive PCR, or real-time PCR. In various embodiments of any of the aspects delineated herein, the detectable nucleic acid probe is fluorogenic. In various embodiments of any of the aspects delineated herein, fluorescence is used to generate a melting curve.

In various embodiments of any of the aspects delineated herein, the sample is a biological fluid or tissue sample derived from a patient. In various embodiments of any of the aspects delineated herein, the sample is one or more of blood, serum, urine, semen and saliva. In various embodiments of any of the aspects delineated herein, the target nucleic acid is derived from a bacterium, a virus, a spore, a fungus, a parasite, a prokaryotic cell, or a eukaryotic cell. In various embodiments of any of the aspects delineated herein, the sample is probed to identify a marker associated with a condition selected from the group consisting of neoplasia, inflammation, pathogen infection, immune response, sepsis, the presence of liver metabolites, and the presence of a genetically modified organism. In various embodiments of any of the aspects delineated herein, marker identification diagnoses a neoplasia, identifies the tissue of origin of the neoplasia, monitors response of the neoplasia to treatment, or predicts the risk of developing a neoplasia. In various embodiments of any of the aspects delineated herein, the eukaryotic cell is a neoplastic cell derived from lung, breast, prostate, thyroid, or pancreas. In particular embodiments, the neoplasia is chronic myelogenous leukemia (CML). In certain embodiments, the target nucleic acid is BCR-ABL.

In various embodiments of any of the aspects delineated herein, the target nucleic acid molecule is derived from a bacterial pathogen selected from the list consisting of *Aerobacter, Aeromonas, Acinetobacter, Actinomyces israelii, Agrobacterium, Bacillus, Bacillus antracis, Bacteroides, Bartonella, Bordetella, Bortella, Borrelia, Brucella, Burkholderia, Calymmatobacterium, Campylobacter, Citrobacter, Clostridium, Clostridium perfringens, Clostridium tetani, Cornyebacterium, Corynebacterium diphtheriae, corynebacterium* sp., *Enterobacter, Enterobacter aerogenes, Enterococcus, Erysipelothrix rhusiopathiae, Escherichia, Francisella, Fusobacterium nucleatum, Gardnerella, Haemophilus, Hafnia, Helicobacter, Klebsiella, Klebsiella pneumoniae, Lactobacillus, Legionella, Leptospira, Listeria, Morganella, Moraxella, Mycobacterium, Neisseria, Pasteurella, Pasteurella multocida, Proteus, Providencia, Pseudomonas, Rickettsia, Salmonella, Serratia, Shigella, Staphylococcus, Stentorophomonas, Streptococcus, Streptobacillus moniliformis, Treponema, Treponema pallidium, Treponema pertenue, Xanthomonas, Vibrio*, and *Yersinia*. In particular embodiments, the bacterial pathogen is antibiotic resistant.

In various embodiments of any of the aspects delineated herein, the target nucleic acid molecule is derived from a virus selected from the list consisting of hepatitis C virus, human immunodeficiency virus, Retrovirus, Picornavirus, polio virus, hepatitis A virus, Enterovirus, human Coxsackie virus, rhinovirus, echovirus, Calcivirus, Togavirus, equine encephalitis virus, rubella virus, Flavivirus, dengue virus, encephalitis virus, yellow fever virus, Coronavirus, Rhabdovirus, vesicular stomatitis virus, rabies virus, Filovirus, ebola virus, Paramyxovirus, parainfluenza virus, mumps virus, measles virus, respiratory syncytial virus, Orthomyxovirus, influenza virus, Hantaan virus, bunga virus, phlebovirus, Nairo virus, Arena virus, hemorrhagic fever virus, reovirus, orbivirus, Rotavirus, Birnavirus, Hepadnavirus, hepatitis B virus, Parvovirus, Papovavirus, papilloma virus, polyoma virus, adenovirus, herpes simplex virus 1, herpes simplex virus 2, varicella zoster virus, cytomegalovirus, herpes virus, variola virus, vaccinia virus, pox virus, African swine fever virus, Norwalk virus, and astrovirus.

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "alteration" is meant an increase or decrease. An alteration may be by as little as 1%, 2%, 3%, 4%, 5%, 10%, 20%, 30%, or by 40%, 50%, 60%, or even by as much as 75%, 80%, 90%, or 100%.

By "amplify" is meant to increase the number of copies of a molecule. In one example, the polymerase chain reaction (PCR) is used to amplify nucleic acids. As used herein, "preamplify" is meant to increase the number of copies of a molecule (e.g., a biomarker or nucleic acid molecule) before exponentially amplifying the molecule. For example, preamplification may involve a linear increase in the number of copies of a molecule.

By "annealing temperature" is meant the highest temperature at which a detection probe or primer binds or hybridizes to a target nucleic acid As used herein, "base analog" refers to a heterocyclic moiety which is located at the 1' position of a nucleotide sugar moiety in a modified nucleotide that can be incorporated into a nucleic acid duplex (or the equivalent position in a nucleotide sugar moiety substitution that can be incorporated into a nucleic acid duplex). In the dsRNAs of the invention, a base analog is generally either a purine or pyrimidine base excluding the common bases guanine (G), cytosine (C), adenine (A), thymine (T), and uracil (U). Base analogs can duplex with other bases or base analogs in dsRNAs. Base analogs include those useful in the compounds and methods of the invention, e.g., those disclosed in U.S. Pat. Nos. 5,432,272 and 6,001,983 to Benner and U.S. Patent Publication No. 20080213891 to Manoharan, which are herein incorporated by reference. Non-limiting examples of bases include hypoxanthine (I), xanthine (X), 3β-D-ribofuranosyl-(2,6-diaminopyrimidine; K), 3-β-D-ribofuranosyl-(1-methyl-pyrazolo[4,3-d]pyrimidine-5,7(4H,6H)-dione; P), iso-cytosine (iso-C), iso-guanine (iso-G), 1-β-D-ribofuranosyl-(5-nitroindole), 1-β-D-ribofuranosyl-(3-nitropyrrole), 5-bromouracil, 2-aminopurine, 4-thio-dT, 7-(2-thienyl)-imidazo[4,5-b]pyridine (Ds) and pyrrole-2-carbaldehyde (Pa), 2-amino-6-(2-thienyl)purine (S), 2-oxopyridine (Y), difluorotolyl, 4-fluoro-6-methylbenzimidazole, 4-methylbenzimidazole, 3-methyl isocarbostyrilyl, 5-methyl isocarbostyrilyl, and 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylindolyl, 4,6-dimethylindolyl, phenyl, napthalenyl, anthracenyl, phenanthracenyl, pyrenyl, stilbenzyl, tetracenyl, pentacenyl, and structural derivatives thereof (Schweitzer et al., J. Org. Chem., 59:7238-7242 (1994); Berger et al., Nucleic Acids Res., 28(15):2911-2914 (2000); Moran et al., J. Am. Chem. Soc., 119:2056-2057 (1997); Morales et al., J. Am. Chem. Soc., 121:2323-2324 (1999); Guckian et al., J. Am. Chem. Soc., 118:8182-8183 (1996); Morales et al., J. Am. Chem. Soc., 122(6):1001-1007 (2000); McMinn et al., J. Am. Chem. Soc., 121:11585-11586 (1999); Guckian et al., J. Org. Chem., 63:9652-9656 (1998); Moran et al., Proc. Natl. Acad. Sci., 94:10506-10511 (1997); Das et al., J. Chem. Soc., Perkin Trans., 1:197-206 (2002); Shibata et al., J. Chem. Soc., Perkin Trans., 1: 1605-1611 (2001); Wu et al., J. Am. Chem. Soc., 122(32):7621-7632 (2000); O'Neill et al., J. Org. Chem., 67:5869-5875 (2002); Chaudhuri et al., J. Am. Chem. Soc., 117:10434-10442 (1995); and U.S. Pat. No. 6,218,108.). Base analogs may also be a universal base.

As used herein, "universal base" refers to a heterocyclic moiety located at the 1' position of a nucleotide sugar moiety in a modified nucleotide, or the equivalent position in a nucleotide sugar moiety substitution, that, when present in a nucleic acid duplex, can be positioned opposite more than one type of base without altering the double helical structure (e.g., the structure of the phosphate backbone). Additionally, the universal base does not destroy the ability of the single stranded nucleic acid in which it resides to duplex to a target nucleic acid. The ability of a single stranded nucleic acid containing a universal base to duplex a target nucleic can be assayed by methods apparent to one in the art (e.g., UV absorbance, circular dichroism, gel shift, single stranded nuclease sensitivity, etc.). Additionally, conditions under which duplex formation is observed may be varied to determine duplex stability or formation, e.g., temperature, as melting temperature (Tm) correlates with the stability of nucleic acid duplexes. Compared to a reference single stranded nucleic acid that is exactly complementary to a target nucleic acid, the single stranded nucleic acid containing a universal base forms a duplex with the target nucleic acid that has a lower Tm than a duplex formed with the complementary nucleic acid. However, compared to a reference single stranded nucleic acid in which the universal base has been replaced with a base to generate a single mismatch, the single stranded nucleic acid containing the universal base forms a duplex with the target nucleic acid that has a higher Tm than a duplex formed with the nucleic acid having the mismatched base.

Some universal bases are capable of base pairing by forming hydrogen bonds between the universal base and all of the bases guanine (G), cytosine (C), adenine (A), thymine (T), and uracil (U) under base pair forming conditions. A universal base is not a base that forms a base pair with only one single complementary base. In a duplex, a universal base may form no hydrogen bonds, one hydrogen bond, or more than one hydrogen bond with each of G, C, A, T, and U opposite to it on the opposite strand of a duplex. Preferably, a universal base does not interact with the base opposite to it on the opposite strand of a duplex. In a duplex, base pairing between a universal base occurs without altering the double helical structure of the phosphate backbone. A universal base may also interact with bases in adjacent nucleotides on the same nucleic acid strand by stacking interactions. Such stacking interactions stabilize the duplex, especially in situations where the universal base does not form any hydrogen bonds with the base positioned opposite to it on the opposite strand of the duplex. Non-limiting examples of universal-binding nucleotides include inosine, 1-β-D-ribofuranosyl-5-nitroindole, and/or 1-β-D-ribofuranosyl-3-nitropyrrole (US Pat. Appl. Publ. No. 20070254362 to Quay et al.; Van Aerschot et al., An acyclic 5-nitroindazole nucleoside analogue as ambiguous nucleoside. Nucleic Acids Res. 1995 Nov. 11; 23(21):4363-70; Loakes et al., 3-Nitropyrrole and 5-nitroindole as universal bases in primers for DNA sequencing and PCR. Nucleic Acids Res. 1995 Jul. 11; 23(13):2361-6; Loakes and Brown, 5-Nitroindole as an universal base analogue. Nucleic Acids Res. 1994 Oct. 11; 22(20):4039-43).

By "binding" is meant having a physicochemical affinity for a molecule. Binding is measured by any of the methods of the invention, e.g., hybridization of a detectable nucleic acid probe, such as a TaqMan based probe, Pleiades based probe.

By "biological sample" is meant any tissue, cell, fluid, or other material derived from an organism (e.g., human subject).

By "complementary" or "complementarity" is meant that a nucleic acid can form hydrogen bond(s) with another nucleic acid sequence by either traditional Watson-Crick or Hoogsteen base pairing. In reference to the nucleic molecules of the present disclosure, the binding free energy for a nucleic acid molecule with its complementary sequence is sufficient to allow hybridization. Determination of binding free energies for nucleic acid molecules is well known in the art (see, e.g., Turner, et al., CSH Symp. Quant. Biol. LII, pp. 123-133, 1987; Frier, et al., Proc. Nat. Acad. Sci. USA 83:9373-9377, 1986; Turner, et al., J. Am. Chem. Soc. 109:3783-3785, 1987). A percent complementarily indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary, respectively). To determine that a percent complementarity is of at least a certain percentage, the percentage of contiguous residues in a nucleic acid molecule that can form hydrogen bonds (e.g., Watson-Crick base pairing) with a second nucleic acid sequence is calculated and rounded to the nearest whole number (e.g., 12, 13, 14, 15, 16, or 17 nucleotides out of a total of 23 nucleotides in the first oligonucleotide being based paired to a second nucleic acid sequence having 23 nucleotides represents 52%, 57%, 61%, 65%, 70%, and 74%, respectively; and has at least 50%, 50%, 60%, 60%, 70%, and 70% complementarity, respectively). As used herein, "substantially complementary" refers to complementarity between the strands such that they are capable of hybridizing under biological conditions. Substantially complementary sequences have 60%, 70%, 80%, 90%, 95%, or even 100% complementarity. Additionally, techniques to determine if two strands are capable of hybridizing under biological conditions by examining their nucleotide sequences are well known in the art.

By "detect" refers to identifying the presence, absence, or level of an agent.

By "detectable" is meant a moiety that when linked to a molecule of interest renders the latter detectable. Such detection may be via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

As used herein, "duplex" refers to a double helical structure formed by the interaction of two single stranded nucleic acids. A duplex is typically formed by the pairwise hydrogen bonding of bases, i.e., "base pairing", between two single stranded nucleic acids which are oriented antiparallel with respect to each other. Base pairing in duplexes generally occurs by Watson-Crick base pairing, e.g., guanine (G) forms a base pair with cytosine (C) in DNA and RNA, adenine (A) forms a base pair with thymine (T) in DNA, and adenine (A) forms a base pair with uracil (U) in RNA. Conditions under which base pairs can form include physiological or biologically relevant conditions (e.g., intracellular: pH 7.2, 140 mM potassium ion; extracellular pH 7.4, 145 mM sodium ion). Furthermore, duplexes are stabilized by slacking interactions between adjacent nucleotides. As used herein, a duplex may be established or maintained by base pairing or by stacking interactions. A duplex is formed by two complementary nucleic acid strands, which may be substantially complementary or fully complementary.

By "fragment" is meant a portion of a nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 5, 10, 15, 20, 30, 40, 50, 60, 70, 80, 90, or 100 nucleotides.

By "half-maximal effective concentration" or "$EC_{50}$" is response halfway between the baseline and maximum of the ratio of target molecule to a reference molecule, which corresponds to the inflection point from a sigmoidal curve fit (e.g logistic curve fit) when the ratio of target molecule to internal standard is plotted against molar ratio of the reference molecule.

Single-stranded nucleic acids that base pair over a number of bases are said to "hybridize." Hybridization is typically determined under physiological or biologically relevant conditions (e.g., intracellular: pH 7.2, 140 mM potassium ion; extracellular pH 7.4, 145 mM sodium ion). Hybridization conditions generally contain a monovalent cation and biologically acceptable buffer and may or may not contain a divalent cation, complex anions, e.g. gluconate from potassium gluconate, uncharged species such as sucrose, and inert polymers to reduce the activity of water in the sample, e.g. PEG. Such conditions include conditions under which base pairs can form.

Hybridization is measured by the temperature required to dissociate single stranded nucleic acids forming a duplex, (i.e., the melting temperature, Tm). Hybridization conditions are also conditions under which base pairs can form. Various conditions of stringency can be used to determine hybridization (see, e.g., Wahl, G. M. and S. L. Berger (1987) Methods Enzymol. 152:399; Kimmel, A. R. (1987) Methods Enzymol. 152:507). Stringent temperature conditions will ordinarily include temperatures of at least about 30° C., more preferably of at least about 37° C., and most preferably of at least about 42° C. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41 (% G+C)-(600/N), where N is the number of bases in the hybrid, and [Na+] is the concentration of sodium ions in the hybridization buffer ([Na+] for 1×SSC=0.165 M). Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Antisense to Molecular Cloning Techniques, 1987, Academic Press, New York); and Sambrook et al., Molecular Cloning: A Laboratory Manual, Cold Spring Harbor Laboratory Press, New York. Varying additional parameters, such as hybridization time, the concentration of detergent, e.g., sodium dodecyl sulfate (SDS), the inclusion or exclusion of carrier DNA, and wash conditions are well known to those skilled in the art. Useful variations on hybridization conditions will be readily apparent to those skilled in the art.

By "increases" is meant a positive alteration of at least 10%, 25%, 50%, 75%, 100%, 200%, 300%, 400%, 500%, 1000%, or more.

By "internal standard" is meant a competitive template or molecule that is amplified in the presence of a native template or molecule.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "gene expression profile" is meant a characterization of the expression or expression level of two or more polynucleotides.

By "logistic curve" is meant a sigmoid curve in which the initial rate or response is approximately exponential, then slows approaching saturation, and stops at saturation. An exemplary logistic response curve, useful in the methods of the invention, is the equation B0+((B1−B0)/(1.0+EXP((B2−fNT)*B3))), where B0=bottom, B1=top, B2=EC50, B3=hill coefficient [IS].

By "marker" or "biomarker" is meant an analyte whose presence, absence, or level is differentially regulated in connection with a disease or condition relative to a reference. Exemplary analytes include polynucleotides, polypeptides, and fragments thereof. For example, BCR-ABL is a biomarker for chronic myelogenous leukemia.

By "match" is meant when a nucleotide is able to base pair with another nucleotide (e.g., to form a double-stranded molecule). Base pairing in duplexes generally occurs by Watson-Crick base pairing, e.g., guanine (G) forms a base pair with cytosine (C) in DNA and RNA, adenine (A) forms a base pair with thymine (T) in DNA, and adenine (A) forms a base pair with uracil (U) in RNA.

By "mismatch" is meant when a nucleotide of one nucleic acid strand is not able to base pair with a nucleotide in the corresponding position of a second nucleotide strand in a duplex. Two nucleic acid strands may still hybridize, even if one, two, three, or more positions have a mismatch. Mismatches can be tolerated so long as there is sufficient complementarity between two nucleic acid sequences.

By "melting temperature" or "Tm" is meant the lowest temperature at which a detection probe or primer does not bind or hybridize to a target nucleic acid. The melting temperature can be determined by the inflection point of melting curve profile, which measures hybridization as a function of temperature. The melting temperature can also be predicted using programs (Epoch uses Major Groove Binders and modified nucleotides to adjust binding Tm). As used herein, "ΔTm" is meant the difference between PCR operating temperatures (e.g., the annealing temperature) and the probe Tm.

By "melting curve" is meant a plot of signal (e.g., fluorescence) over a temperature range that includes the annealing temperature and the melting temperature.

By "neoplasia" is meant a disease or disorder characterized by excess proliferation or reduced apoptosis. Illustrative neoplasms for which the invention can be used include, but are not limited to leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

As used herein, the term "nucleic acid" refers to deoxyribonucleotides, ribonucleotides, or modified nucleotides, and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

By "native" is meant endogenous, or originating in a sample.

As used herein a "nucleic acid or oligonucleotide probe" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. It will be understood by one of skill in the art that probes may bind target sequences lacking complete complementarity with the probe sequence depending upon the stringency of the hybridization conditions. The probes are preferably directly labeled with isotopes, for example, chromophores, lumiphores, chromogens, or indirectly labeled with biotin to which a streptavidin complex may later bind. By assaying for the presence or absence of the probe, one can detect the presence or absence of a target gene of interest.

As used herein, "nucleotide" is used as recognized in the art to include those with natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see, e.g., Usman and McSwiggen, supra; Eckstein, et al., International PCT Publication No. WO 92/07065; Usman et al, International PCT Publication No. WO 93/15187; Uhlman & Peyman, supra, all are hereby incorporated by reference herein). There are several examples of modified nucleic acid bases known in the art as summarized by Limbach, et al, Nucleic Acids Res. 22:2183, 1994. Some of the non-limiting examples of base modifications that can be introduced into nucleic acid molecules include, hypoxanthine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin, et al., Biochemistry 35:14090, 1996; Uhlman & Peyman, supra).

By "modified bases" is meant nucleotide bases other than adenine, guanine, cytosine and uracil at 1' position or their equivalents.

As used herein, "modified nucleotide" refers to a nucleotide that has one or more modifications to the nucleoside, the nucleobase, pentose ring, or phosphate group. For example, modified nucleotides exclude ribonucleotides containing adenosine monophosphate, guanosine monophosphate, uridine monophosphate, and cytidine monophosphate and deoxyribonucleotides containing deoxyadenosine monophosphate, deoxyguanosine monophosphate, deoxythymidine monophosphate, and deoxycytidine monophosphate. Modifications include those naturally occurring that result from modification by enzymes that modify nucleotides, such as methyltransferases. Modified nucleotides also include synthetic or non-naturally occurring nucleotides. Synthetic or non-naturally occurring modifications in nucleotides include those with 2' modifications, e.g., 2'-methoxyethoxy, 2'-fluoro, 2'-allyl, 2'-O-[2-(methylamino)-2-oxoethyl], 4'-thio, 4'-CH$_2$—O-2'-bridge, 4'-(CH$_2$)$_2$—O-2'-bridge. 2'-LNA, and 2'—O—(N-methylcarbamate) or those comprising base analogs. In connection with 2'-modified nucleotides as described for the present disclosure, by "amino" is meant 2'-NH$_2$ or 2'-O—NH$_2$, which can be modified or unmodified. Such modified groups are described, e.g., in Eckstein, et al., U.S. Pat. No. 5,672,695 and Matulic-Adamic, et al., U.S. Pat. No. 6,248,878.

By "reduces" is meant a negative alteration of at least 10%, 25%, 50%, 75%, or 100%.

By "reference" is meant a standard or control condition. As is apparent to one skilled in the art, an appropriate reference is where one element is changed in order to determine the effect of the one element. In the methods of the invention, a reference nucleic acid molecule (internal standard) is competitively amplified with a target nucleic acid molecule (native template). The internal standard has substantial sequence identity with the native template.

By "secondary structure" or "nucleic acid secondary structure" is meant the intramolecular interaction of a nucleic acid molecule. Typically, secondary structure is due to base-pairing interactions in the nucleic acid molecule, resulting in duplex formation. Exemplary secondary structures include stem-loop and pseudoknot structures. A stem-loop structure occurs when two regions of the same nucleic acid strand, usually complementary in nucleotide sequence when read in opposite directions, base-pair to form a double helix that ends in an unpaired loop. A pseudoknot structure contains at least two stem-loop structures in which half of one stem is intercalated between the two halves of another stem.

The phrase "selectively (or specifically) hybridizes to" refers to the binding, duplexing, or hybridizing of a molecule only to a particular nucleotide sequence under stringent hybridization conditions when that sequence is present in a complex mixture (for example, total cellular or library DNA or RNA).

By "standardized mixture of internal standards" is meant a mixture that contains internal standards having a defined concentration or a defined number of molecules of the internal standards.

By "subject" is meant a mammal, including, but not limited to, a human or non-human mammal, such as a bovine, equine, canine, ovine, or feline.

By "yield" or "yield signal" is meant the maximum amount of signal from the detection of a nucleic acid molecule.

By "target nucleic acid molecule" is meant a nucleic acid or biomarker of the sample that is to be detected or measured, and/or amplified. The target nucleic acid may be any nucleic acid to be amplified, without particular limitation. Examples of target nucleic acids include various types of genes of animals and plants, various virus genes, and various microorganism genes, such as bacteria, mold, and yeast genes, regardless of whether or not they are DNA or RNA. Target nucleic acids may be naturally occurring or artificially synthesized, and an example thereof is PNA. Also, examples include single-stranded nucleic acids and double-stranded nucleic acids. In the present invention, the term "template nucleic acid" refers to an original target of detection that comprises in its molecules a target sequence and serves as a base for primer design.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 91%, 92%, 93%, 94%, 95%, 96%, 97%, 98%, 99%, or even 100% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A is a graph depicting the Fraction NT (y-axis) measurements (closed circles) relative to the input IS:NT ratio (x-axis). The EC50 of this curve was not at 0.0 as expected, but 1.66 (45-fold IS:NT). A scaled melting curve to correct data for fluorescent yield difference was generated (open circles). FIG. 1B is a graph of IS and NT melting curves that suggested a possible source of error to be a 3-fold fluorescent yield difference between IS and NT melting curves (i.e., given equal molecules of template, IS generates lower fluorescent signal than NT). However, the fluorescent yield difference did not entirely account for the observed EC50 shift in FIG. 1A.

FIG. 2A is a graph depicting a series of melting curves that assume the fluorescence signal of IS alone and NT alone are equal (equal fluorescent efficiency). FIG. 2B is a graph simulating response curves observed in some hybridization probes, where the IS has a lower the fluorescent signal relative to NT (a quarter the fluorescent efficiency). The fraction NT calculated using a two-sigmoid curve fit generated a shift in EC50, which can be corrected by scaling the signal according to the difference in fluorescent efficiency. This modeling indicates that if an EC50 shift is due to a lower probe quantum yield, it can be corrected by scaling the IS signal.

FIG. 3A is a graph showing that IS template engineered to eliminate secondary structure produced IS:NT results closer to the expected ratio than the original IS template IS3. The IS3 melting curve at a 2:1 IS:NT amplicon provided an inaccurate melting curve ratio of 1:4 (closed circles). The IS19 melting curve (open circles) produced a 1:1 IS:NT result, that was closer to the expected 2:1 ratio than that indicated by the IS3 melting curve. FIG. 3B is a graph that indicates both IS19 and IS20 produced responses closer to the expected value over the entire range of IS:NT ratios. IS3 (solid squares) did not yield responses reflective of the expected values over the indicated IS:NT amplicon ratios. Both IS19 (open circles) and IS20 (open triangles) produced responses closer to the expected value over the entire range of IS:NT ratios. These results indicate that secondary structure in the IS probe binding site can distort the melting curve response.

DETAILED DESCRIPTION OF THE INVENTION

Figure 1A:
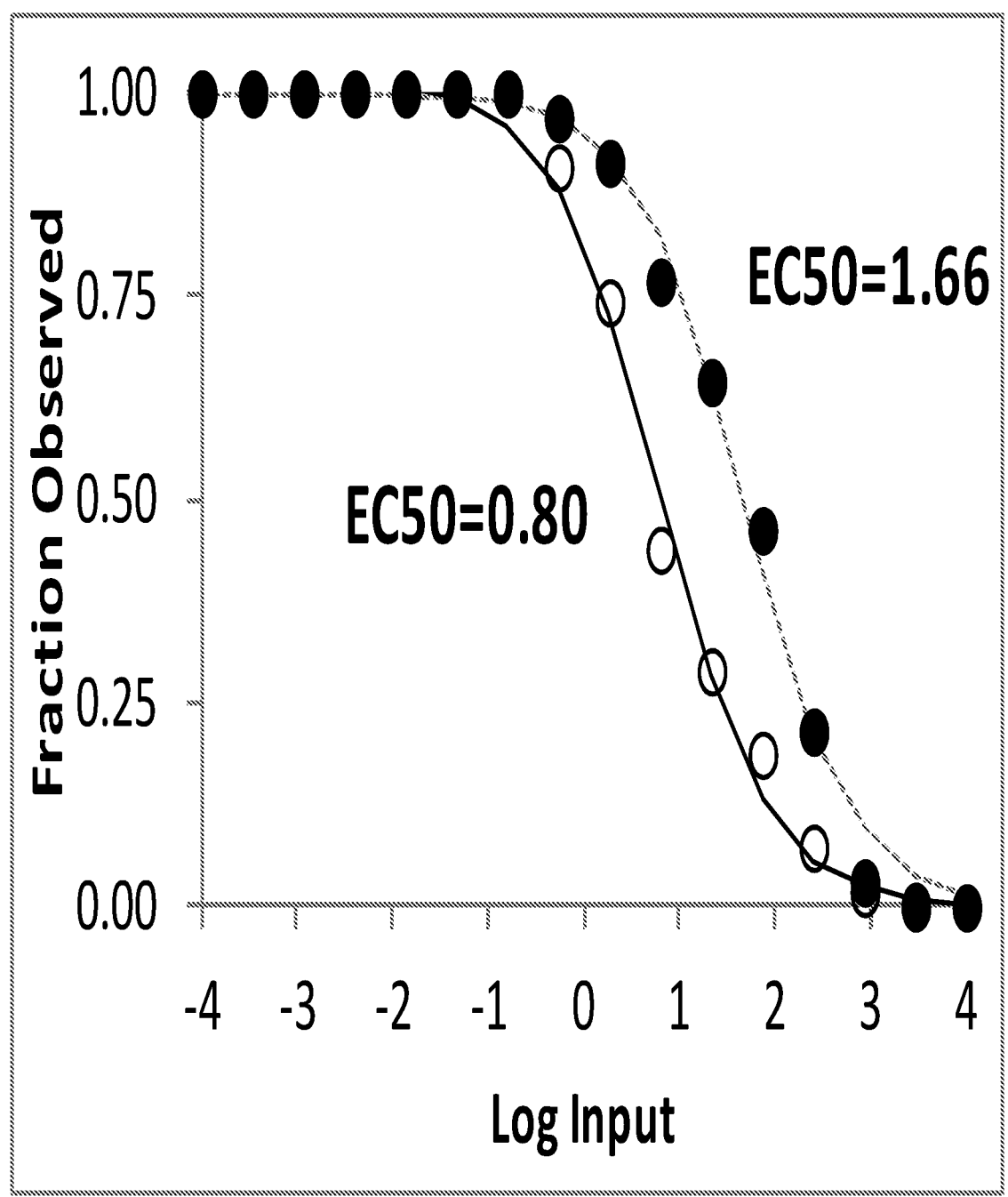
FIGS. 1A and 1B depict that SNAQ measurements can be inaccurate. Serial dilutions of IS amplicon were mixed with a fixed quantity of NT, amplified by PCR and measured by melting curve analysis.

As described below, the present invention features compositions and methods that provide for quantitative PCR that reduces the effect of yield difference between detection of the target nucleic acid molecule (i.e., native template; NT) and reference nucleic acid molecule (i.e., internal standard; IS) and enhances the accuracy of target nucleic acid quantitation in a sample (e.g., a biologic sample).

Advantageously, the present invention provides for the quantitative measurement of the amount of native template in a sample when the native template is amplified in the presence of a hybridization probe (e.g., a detectable probe in real-time PCR) and an internal standard, and minimizes the effect of a difference in signal yield between native template and internal standard. Detection and measurement of nucleic acid molecules in accordance with the methods of the invention are useful for the diagnosis, monitoring, or characterization of virtually any disease characterized by an alteration in gene expression including, for example, neoplasia, inflammation, and a variety of infectious diseases.

The invention is based, at least in part, on the discovery that differences in fluorescent yield between native template and internal standard amplification products has the potential to decrease the accuracy of target nucleic acid quantitation in quantitative PCR (qPCR). Thus, adjusting for yield difference increases the accuracy of the quantitation of native template. It has been found that fluorescent yield is influenced in part by nucleic acid secondary structure (e.g., stem-loop structure) in one or more of the native template and internal standard nucleic acid molecules. Without being bound to a particular theory, secondary structure reduces binding of fluorescent probe to template during competitive PCR. Thus, it is an object of the present invention to provide a method that allows accurate quantitation where the signal yield between native template and internal standard differs.

The present invention provides a method for nucleic acid quantitation using a competitive amplification reaction that adjusts or reduces a difference in signal yield between native template and internal standard. Various means are provided for addressing this effect, without limitation. In one embodiment, probe binding sites or alternative probe binding sites are selected without secondary structure differences in one or more of the native template and internal standard. In an additional embodiment, an internal standard is selected or designed that reduces or eliminates existing secondary structure in the probe binding site of one or more of the native template and internal standard. This may be achieved by one or more nucleic acid base alterations in native template or internal standard nucleic acid molecules. It is preferable to avoid creating secondary structure with base pair changes in the internal standard. In another embodiment, one or more primer binding sites may be selected or designed to reduce or eliminate secondary structure in one or more of the native template and internal standard. In yet another embodiment, algorithms (e.g., a curve fitting algorithm) are used to scale the yield signal of the native template and internal standard amplification products and/or reduce the difference in yield signal between the native template and internal standard amplification products. Where a difference in yield signal results from the effects of secondary structure, the response curve bias may be corrected or adjusted using a curve fitting algorithm (e.g., a logistic curve fitting algorithm). Combinations of any of the above may be used to reduce the effect of a difference in yield signal between the native template and internal standard. With this approach, measurement is quantitative and instrument-to-instrument variation is minimized when measured at endpoint.

Assay System

In one aspect, the endpoint amplification product for a target nucleic acid is quantified relative to a known number of molecules of its respective internal standard within the standardized mixture of internal standards. For example, sample aliquots are added to a series of tubes (2, 3, 4, 5, 6, 7, 8, 9, 10) containing increasing numbers of copies of synthetic competitive template internal standard, and primers. Each primer pair coamplifies a native template and its respective competitive internal standard template with equal efficiency. Gene measurements are normalized to a coamplified reference gene that controls for known sources of variation, including inter-sample variation in loading due to pipetting, interfering substances such as PCR inhibitors, inter-gene variation in amplification efficiency, and false negatives. Recent reports have described the successful use of such a method to measure the gene expression of several promising biomarkers in samples of blood (Rots et al., Leukemia 2000 December; 14(12):2166-75; Peters et al., Clin Chem 2007 June; 53(6):1030-7) or other tissues. StaRT-PCR has been used successfully to identify patterns of gene expression associated with diagnosis of lung cancer (Warner et al., J Mol Diagn 2003 August; 5(3):176-83), risk of lung cancer (Crawford et al., Carcinogenesis 2007 December: 28(12):2552-9), pulmonary sarcoidosis (Allen et al., Am J Respir Cell Mol Biol 1999 December; 21(6):693-700), cystic fibrosis (Loitsch et al., Clin Chem 1999 May; 45(5): 619-24), chemoresistance in lung cancer (Harr et al., Mol Cancer 2005; 4:23; Weaver et al., Mol Cancer 2005:4(1):18) childhood leukemias (Rots et al., Leukemia 2000 December; 14(12):2166-75), staging of bladder cancer (Mitra et al., BMC Cancer 2006; 6:159), and to develop databases of normal range of expression of inflammatory genes in peripheral blood samples (Peters et al., Clin Chem 2007 June; 53(6):1030-7).

Primers

The primers of the invention embrace oligonucleotides of sufficient length and appropriate sequence so as to provide specific initiation of polymerization on a significant number of nucleic acids in the polymorphic locus. Specifically, the term "primer" as used herein refers to a sequence comprising two or more deoxyribonucleotides or ribonucleotides, preferably more than three, and most preferably more than 8, which sequence is capable of initiating synthesis of a primer extension product, which is substantially complementary to a polymorphic locus strand. The primer must be sufficiently long to prime the synthesis of extension products in the presence of the inducing agent for polymerization. The exact length of primer will depend on many factors, including temperature, buffer, and nucleotide composition. The oligonucleotide primer typically contains between 12 and 27 or more nucleotides, although it may contain fewer nucleotides. Primers of the invention are designed to be "substantially" complementary to each strand of the genomic locus to be amplified and include the appropriate G or C nucleotides as discussed above. This means that the primers must be sufficiently complementary to hybridize with their respective strands under conditions that allow the agent for polymerization to perform. In other words, the primers should have sufficient complementarity with the 5' and 3' flanking sequences to hybridize therewith and permit amplification of the genomic locus. In various embodiments, one or more primer binding sites may be selected or designed to reduce or eliminate secondary structure in one or more of the native template and internal standard. While exemplary primers are provided herein, it is understood that any primer that hybridizes with the target sequences of the invention are useful in the method of the invention for detecting a target nucleic acid.

The target nucleic acid may be present in a sample, e.g. clinical samples and biological samples. If high quality clinical samples are not used, amplification primers are designed to recognize shorter target sequences. Primer Tm is about 60+/−1° C. Amplification primers are compared by homology against known sequences to ensure the binding specificity. Despite the use of DNAse in the RNA purification protocol, when possible, primers are designed to span RNA intron/exon splice junctions. Therefore, amplification of genomic contaminants will be inhibited by failure to produce full length products (typically >6 KB).

Internal Standard (IS)

For each target nucleic acid molecule or biomarker, the respective synthetic internal standard will match the native template in all but 1, 2, or 3 nucleotides within the probe binding sequence of the native nucleic acid molecule or biomarker. The probe sequence for the internal standard will be based on this rearrangement, and therefore is predicted to bind only to the internal standard sequence, but not the corresponding native template. Internal standards are formulated into a mixture that contains the internal standards at a defined concentration or number of molecule of the internal standards. For example, such internal standards are also referred to as a "defined reference nucleic acid molecule", having a known concentration of the nucleic acid molecule or a known number of nucleic acid molecules.

Synthetic template oligo internal standards with mutations in the probe binding site that lower the IS binding Tm by 15° C.±3° C. are designed. A sequence analysis program (e.g., DINAMelt Server (Markham et al. Nucleic Acids Res 2005 (Web Server issue) 33:W577-W581)) is used to select the appropriate IS mutations. The metric for determining the successful probe and IS design is the signal-to-noise ratio (S/N) in the assay. The S/N of each assay is measured comparing the signals generated by four replicates of pure NT vs. pure IS samples.

It has been discovered that fluorescent yield is influenced in part by nucleic acid secondary structure (e.g., stem-loop structure) in one or more of the native template and internal standard nucleic acid molecules. Without being bound to a particular theory, secondary structure reduces binding of fluorescent probe to template during competitive PCR. According to the methods of the invention, secondary structure should be minimized or eliminated in the internal standard. Using single strand DNA folding prediction algorithms can be used to detect the stem loop. At Tm, a complete stem loop should have a predicted dG of >0.5, preferably >1.0, preferably >2.0. At Tm, a half stem loop (probe binding site contacts half of the stem loop), should have a dG>0.0, preferably >0.5, preferably >1.0.

In various embodiments, probe binding sites or alternative probe binding sites are selected without secondary structure differences in one or more of the native template and internal standard. In additional embodiments an internal standard is selected or designed that reduces or eliminates existing secondary structure in the probe binding site of one or more of the native template and internal standard. This may be achieved by one or more nucleic acid base alterations in native template or internal standard nucleic acid molecules. It is preferable to avoid creating secondary structure with base pair changes in the internal standard.

Probe

A PCR product (i.e., amplicon) or real-time PCR product is detected by probe binding. Probes (e.g., non hydrolyzable fluorescent) probes are designed to native template Tm. The metric for determining the successful probe and IS design is the signal-to-noise ratio (S/N) in the assay. The S/N of each assay is measured comparing the signals generated by four replicates of pure NT vs. pure IS samples.

In one embodiment, probe binding generates a fluorescent signal, for example, by coupling a fluorogenic dye molecule and a quencher moiety to the same or different oligonucleotide substrates (e.g., TaqMan® (Applied Biosystems, Foster City, Calif., USA), Pleiades (Nanogen, Inc., Bothell, Wash., USA), Molecular Beacons (see, for example, Tyagi et al., Nature Biotechnology 14(3):303-8, 1996), Scorpions® (Molecular Probes Inc., Eugene, Oreg., USA)). In another example, a PCR product is detected by the binding of a fluorogenic dye that emits a fluorescent signal upon binding (e.g., SYBR® Green (Molecular Probes)). Such detection methods are useful for the detection of a target specific PCR product.

Quantitation

Following PCR, the concentration of the native template is calculated from the ratio (native template:internal standard template) versus known copies of internal standard included in the reaction. Gene measurements are normalized to a coamplified reference gene to control for known sources of variation, including inter-sample variation in loading due to pipetting, interfering substances, such as PCR inhibitors, inter-gene variation in amplification efficiency, and false negatives.

In various embodiments, algorithms (e.g., a curve fitting algorithm) are used to scale the yield signal of the native template and internal standard amplification products and/or reduce the difference in yield signal between the native template and internal standard amplification products. Where a difference in yield signal results from the effects of secondary structure, the response curve bias may be corrected or adjusted using a curve fitting algorithm (e.g., a logistic curve fitting algorithm). Combinations of any of the above may be used to reduce the effect of a difference in yield signal between the native template and internal standard.

In particular embodiments, target nucleic acid amplification further comprises a preamplification step. The use of the preamplification step markedly reduces the amounts of starting sample (e.g., cDNA) and reagents required for each PCR reaction. Measuring each gene relative to a known number of internal standard molecules within a standardized mixture of internal standards in each reaction controls for unpredictable inter-sample variation in the efficiency of pre-amplification caused by reagent consumption, PCR inhibitors, and/or product inhibition. A standardized mixture of internal standards controls for preferential amplification of one transcript over another due to differences in amplification efficiencies. The use of nanofluidic technology in combination with pre-amplification with multiple sets of primers and internal standards in the same reaction provides for the measurement of many genes (>100) using the RNA quantity normally required for six measurements. This allows for higher throughput that is virtually unrestricted by RNA input.

Polymerase Chain Reaction (PCR) and PCR Kinetics

The polymerase chain reaction (PCR) is a technique of amplifying or synthesizing large quantities of a target DNA segment. PCR is achieved by separating the DNA into its two complementary strands, binding a primer to each single strand at the end of the given DNA segment where synthesis starts, and adding a DNA polymerase to synthesize the complementary strand on each single strand having a primer bound thereto. The process is repeated until a sufficient number of copies of the selected DNA segment have been synthesized.

During a typical PCR reaction, double stranded DNA is separated into single strands by raising the temperature of the DNA containing sample to a denaturing temperature where the two DNA strands separate (i.e. the "melting temperature of the DNA") and then the sample is cooled to a lower temperature that allows the specific primers to attach (anneal), and replication to occur (extend). In illustrated embodiments, a thermostable polymerase is utilized in the polymerase chain reaction, such as Taq DNA Polymerase and derivatives thereof, including the Stoffel fragment of Taq DNA polymerase and KlenTaq1 polymerase (a 5'-exonuclease deficient variant of Taq polymerase—see U.S. Pat. No. 5,436,149); Pfu polymerase; Tth polymerase; and Vent polymerase.

PCR has a sensitivity five orders of magnitude better than the best blotting procedures. This sensitivity makes PCR desirable as a quantitative tool. However, the use of a system undergoing exponential amplification is not ideally suited to quantification. Small differences between sample sizes can become huge difference in results when they are amplified through 20-40 cycles.

A typical PCR reaction profile has three segments: an early lag phase, an exponential growth phase, and a plateau. The lag phase is mainly a reflection of the sensitivity of the instrument and the background signal of the probe system used to detect the PCR product. The exponential growth phase begins when sufficient product has accumulated to be detected by the instrument. During this "log" phase the amplification course is described by the equation $T_n=T_o(E)_n$, where Tn is the amount of target sequence at cycle n, $T_o$ is the initial amount of target, and E is the efficiency of amplification. Finally, in the plateau phase, the amplification efficiency drops off extremely rapidly. Product competes more and more effectively with primers for annealing and the amount of enzyme becomes limiting. The exponential equation no longer holds in the plateau phase.

Most of the quantitative information is found in the exponential cycles, but the exponential cycles typically comprise only 4 or 5 cycles out of 40. With traditional PCR methods, finding these informative cycles requires that the reaction be split into multiple reaction tubes that are assayed for PCR product after varying numbers of cycles. This requires either assaying many tubes, or a fairly good idea of the answer before the experiment is begun. Once the position of the exponential phase is determined, the experimental phase can be compared to known standards and the copy number can be calculated.

Competitive Quantitative PCR

Competitive quantitative PCR methods were developed to attempt to overcome difficulties associated with finding the exponential phase of the reaction and to obtain greater precision. A competitor sequence is constructed that is amplified using the same primers as are used to amplify the target sequence. Competitor and target are differentiated, usually by length or internal sequence, and the relative amount of competitor and target are measured after amplification. If the target and the competitor are amplified with equal efficiency, then their ratio at the end of the reaction will be the same as the ratio had been at the beginning. This holds true even into the plateau phase as long as both decline in efficiency at the same rate. Thus, finding the exponential region is no longer a problem. Providing standards in the same tubes with the unknown targets allows for additional control not possible with kinetic methods. For example, adding the competitor before mRNA purification would control for variations in sample preparation and reverse transcription.

The use of currently available competitive PCR techniques continues to suffer from several deficiencies. Firstly, the competitor sequence must be constructed to be as similar as possible to the target sequence with regard to the efficiency of amplification, yet the two sequences must be distinguishable from one another. If the competitor is too close in sequence to the target, heteroduplexes form during the PCR that skew the ratio of the product to the template.

In addition, competitor must be added to the unknown sample at a concentration approximating that of the target. If one product reaches plateau before the other rises above background, no quantitative information can be obtained from that sample. Usually an unknown sample is split and mixed with multiple concentrations of competitor.

Other concerns have been raised regarding competitive quantification methods. A common criticism is that despite all efforts, the target and the competitor together in a sample may be amplified at different efficiencies, even if target and competitor are amplified at the same efficiencies when amplified separately (the obvious control). When the target and competitor are combined in one vessel and the reagents are limiting, the efficiencies of the two amplification reactions may change at different rates. Length differences between target and competitor are of most concern here as the longer product may compete more effectively with the primers and may be more affected by reagent limitations. Both of these concerns could be addressed by making the target and competitor sufficiently alike, if it were not for the problem of forming heteroduplexes during the PCR reaction.

Real-Time Quantitative PCR

Developments in instrumentation have now made real-time monitoring of PCR reactions possible and thus have made the problem of finding the log phase of the reaction trivial.

Thermocycling may be carried out using standard techniques known to those skilled in the art, including the use of rapid cycling PCR. Rapid cycling techniques are made possible by the use of high surface area-to-volume sample containers such as capillary tubes. The use of high surface area-to-volume sample containers allows for a rapid temperature response and temperature homogeneity throughout the biological sample. Improved temperature homogeneity also increases the precision of any analytical technique used to monitor PCR during amplification.

In accordance with an illustrated embodiment of the present invention, amplification of a nucleic acid sequence is conducted by thermal cycling the nucleic acid sequence in the presence of a thermostable DNA polymerase using the device and techniques described in U.S. Pat. No. 5,455,175, the disclosure of which is expressly incorporated herein. In accordance with the present invention, PCR amplification of one or more targeted regions of a DNA sample is conducted while the reaction is monitored by fluorescence.

The first use of fluorescence monitoring at each cycle for quantitative PCR was developed by Higuchi et al., "Simultaneous Amplification and Detection of Specific DNA Sequences," Bio. Technology, 10:413-417, 1992, and used ethidium bromide as the fluorescent entity. Fluorescence was acquired once per cycle for a relative measure of product concentration. The cycle where observable fluorescence first appeared above the background fluorescence (the threshold) correlated with the starting copy number, thus allowing the construction of a standard curve. Probe-based fluorescence detection system dependent on the 5'-exonuclease activity of the polymerase has improved the real-time kinetic method by adding sequence specific detection.

The amplified target may be detected using a TaqMan fluorescent dye to quantitatively measure fluorescence. The TaqMan probe has a unique fluorescently quenched dye and specifically hybridizes to a PCR template sequence, as described by Livak et al., "Allelic discrimination using fluorogenic probes and the 5' nuclease assay," Genet Anal. 1999 February; 14(5-6):143-9.), which is incorporated by reference in its entirety. During the PCR extension phase, the hybridized probe is digested by the exonuclease activity of the Taq polymerase, resulting in release of the fluorescent dye specific for that probe.

The amplified target may also be detected using a Pleiades fluorescent probe detection assay to quantitatively measure fluoresence The Pleiades probe specifically hybridizes to a target DNA sequence and has a fluorescent dye at the 5' terminus which is quenched by the interactions of a 3' quencher and a 5' minor groove binder (MGB), when the probe is not hybridized to the target DNA sequence, as described by Lukhtanov et al., "Novel DNA probes with low background and high hybridization-triggered fluorescence," Nucl. Acids. Res. 2007 January; 35(5):e30), which is incorporated by reference in its entirety. By the end of PCR, the fluorescent emissions from the released dyes reflect the molar ratio of the sample. Methods for assaying such emissions are known in the art, and described, for example, by Fabienne Hermitte, "Mylopreliferative Biomarkers", Molecular Diagnostic World Congress, 2007.

Alternatively, PCR amplification of one or more targeted regions of a DNA sample can be conducted in the presence of fluorescently labeled hybridization probes, wherein the probes are synthesized to hybridize to a specific locus present in a target amplified region of the DNA. In an illustrated embodiment, the hybridization probe system comprises two oligonucleotide probes that hybridize to adjacent regions of a DNA sequence wherein each oligonucleotide probe is labeled with a respective member of a fluorescent energy transfer pair. In this embodiment, the presence of the target nucleic acid sequence in a biological sample is detected by measuring fluorescent energy transfer between the two labeled oligonucleotides.

These instrumentation and fluorescent monitoring techniques have made kinetic PCR significantly easier than traditional competitive PCR. More particularly, real-time PCR has greatly improved the ease, accuracy, and precision of quantitative PCR by allowing observation of the PCR product concentration at every cycle. In illustrated embodiments of the present invention, PCR reactions are conducted using the LIGHTCYCLER® (Roche Diagnostics), a real-time PCR instrument that combines a rapid thermal cycler with a fluorimeter. Through the use of this device, the PCR product is detected with fluorescence, and no additional sample processing, membrane arrays, gels, capillaries, or analytical tools are necessary. Other PCR instrumentation, as known in the art, may be used in the practice of the present invention.

Diagnostic Methods

The present invention can be employed to measure gene expression or a gene expression profile in a biological sample. Desirably, the methods of the invention require much less starting material than conventional diagnostic methods and may be employed to measure gene expression of biomarkers in blood or other tissues. Accordingly, the invention provides for the identification of patterns of gene expression useful in virtually any clinical setting where conventional methods of analysis are used. For example, the present methods provide for the analysis of biomarkers associated with lung cancer (Warner et al., J Mol Diagn 2003; 5: 176-83), risk of lung cancer (Crawford et al., Cancer Res 2000; 60:1609-18, pulmonary sarcoidosis (Allen et al., Am. J. Respir. Cell. Mol. Biol. 1999:21, 693-700), cystic fibrosis (Loitsch et al., Clin. Chem. 1999:45, 619-624), chemoresistance in lung cancer (Weaver et al., Molecular Cancer, 4, 18, 2005; Harr et al., Molecular Cancer, 4, 23, 2005) childhood leukemias (Rots et al, Leukemia, 14, 2166-2175, 2000), staging of bladder cancer (Mitra et al., BMC Cancer 2006; 6:159), and to develop databases of normal range of expression of inflammatory genes in peripheral blood samples (Peters et al., Clinical Chemistry 53: 1030-1037, 2007).

In one embodiment, the biologic sample is a tissue sample that includes cells of a tissue or organ (e.g., lung, breast, prostatic tissue cells). Such tissue is obtained, for example, from a biopsy of the tissue or organ. In another embodiment, the biologic sample is a biologic fluid sample. Biological fluid samples include blood, blood serum, plasma, urine, seminal fluids, and ejaculate, or any other biological fluid useful in the methods of the invention. Alternatively, the tissue sample is a cytologic fine needle aspirate biopsy or formalin fixed paraffin embedded tissue. Use of the methods of the invention is particularly advantageous for such samples, where RNA often is limited by sample size or degradation.

Diagnostic Assays

The present invention provides a number of diagnostic assays that are useful for detecting or measuring a target nucleic acid molecule in a biological sample. In particular, the invention provides methods for the detection of alterations in gene expression associated with neoplasia (e.g., BCR-ABL in chronic myelogenous leukemia). In particular embodiments, the invention provides for the detection of genes listed in Table 1 (below).

TABLE 1

Exemplary Target Genes for Detection of Neoplasia

| Gene | UniGeneID |
| --- | --- |
| BCR-ABL | Hs.517461; Hs.715409 |
| ERBB3 | Hs.18681 |
| LCK | Hs.470627 |
| DUSP6 | Hs.298654 |
| STAT1 | Hs.470943 |
| MMD | Hs.463483 |
| CPEB4 | Hs.127126 |
| RNF4 | Hs.66394 |
| STAT2 | Hs.530595 |
| NF1 | Hs.113577 |
| FRAP1 | Hs.338207 |
| DLG2 | Hs.503453 |
| IRF4 | Hs.401013 |
| ANXA5 | Hs.480653 |
| HMMR | Hs.72550 |
| HGF | Hs.396530 |
| ZNF264 | Hs.515634 |

Alternatively, the invention provides for the detection and diagnosis of a pathogen in a biological sample. A variety of bacterial and viral pathogens may be detected using the system and methods of the invention. Exemplary bacterial pathogens include, but are not limited to, *Aerobacter, Aeromonas, Acinetobacter, Actinomyces israelli, Agrobacterium, Bacillus, Bacillus antracis, Bacteroides, Bartonella, Bordetella, Bortella, Borrelia, Brucella, Burkholderia, Calymmatobacterium, Campylobacter, Citrobacter, Clostridium, Clostridium perfringens, Clostridium tetani, Cornyebacterium, Corynebacterium diphtheriae, corynebacterium* sp., *Enterobacter, Enterobacter aerogenes, Enterococcus, Erysipelothrix rhusiopathiae, Escherichia, Francisella, Fusobacterium nucleatum, Gardnerella, Haemophilus, Hafnia, Helicobacter, Klebsiella, Klebsiella pneumoniae, Lactobacillus, Legionella, Leptospira, Listeria, Morganella, Moraxella, Mycobacterium, Neisseria, Pasteurella, Pasteurella multocida, Proteus, Providencia, Pseudomonas, Rickettsia, Salmonella, Serratia, Shigella, Staphylococcus, Stentorophomonas, Streptococcus, Streptobacillus moniliformis, Treponema, Treponema pallidium, Treponema pertenue, Xanthomonas, Vibrio,* and *Yersinia.*

Examples of viruses detectable using the system and methods of the invention include Retroviridae (e.g. human immunodeficiency viruses, such as HIV-1 (also referred to as HDTV-III, LAVE or HTLV-III/LAV, or HIV—III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of pathogenic fungi include, without limitation, *Alternaria, Aspergillus, Basidiobolus, Bipolaris, Blastoschizomyces, Candida, Candida albicans, Candida krusei, Candida glabrata* (formerly called *Torulopsis glabrata*), *Candida parapsilosis, Candida tropicalis, Candida pseudotropicalis, Candida guilliermondii, Candida dubliniensis,* and *Candida lusitaniae, Coccidioides, Cladophialophora, Cryptococcus, Cunninghamella, Curvularia, Exophiala, Fonsecaea, Histoplasma, Madurella, Malassezia, Plastomyces, Rhodotorula, Scedosporium, Scopulariopsis, Sporobolomyces, Tinea,* and *Trichosporon*.

Parasites can be classified based on whether they are intracellular or extracellular. An "intracellular parasite" as used herein is a parasite whose entire life cycle is intracellular. Examples of human intracellular parasites include *Leishmania, Plasmodium, Trypanosoma cruzi, Toxoplasma gondii, Babesia,* and *Trichinella spiralis*. An "extracellular parasite" as used herein is a parasite whose entire life cycle is extracellular. Extracellular parasites capable of infecting humans include *Entamoeba histolytica, Giardia lamblia, Enterocytozoon bieneusi, Naegleria* and *Acanthamoeba* as well as most helminths. Yet another class of parasites is defined as being mainly extracellular but with an obligate intracellular existence at a critical stage in their life cycles. Such parasites are referred to herein as "obligate intracellular parasites". These parasites may exist most of their lives or only a small portion of their lives in an extracellular environment, but they all have at least one obligate intracellular stage in their life cycles. This latter category of parasites includes *Trypanosoma rhodesiense* and *Trypanosoma gambiense, Isospora, Cryptosporidium, Eimeria, Neospora, Sarcocystis,* and *Schistosoma*. In one aspect, the invention relates to the prevention and treatment of infection resulting from intracellular parasites and obligate intracellular parasites which have at least in one stage of their life cycle that is intracellular. In some embodiments, the invention is directed to the prevention of infection from obligate intracellular parasites which are predominantly intracellular. An exemplary and non-limiting list of parasites for some aspects of the invention include *Plasmodium* spp. such as *Plasmodium falciparum, Plasmodium malariae, Plasmodium ovale,* and *Plasmodium vivax* and *Toxoplasma gondii*. Blood-borne and/or tissues parasites include *Plasmodium* spp., *Babesia microti, Babesia divergens, Leishmania tropica, Leishmania* spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*. Blood-borne and/or tissues parasites include *Plasmodium, Babesia microti, Babesia divergens, Leishmania tropica, Leishmania, Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*.

Kits

The invention also provides kits for the detection of gene expression. Such kits are useful for the diagnosis, characterization, or monitoring of a neoplasia in a biological sample obtained from a subject (e.g., CML). Alternatively, the invention provides for the detection of a pathogen gene or genes in a biological sample. In various embodiments, the kit includes at least one primer pair that identifies a target sequence, together with instructions for using the primers to identify a gene expression profile in a biological sample. Preferably, the primers are provided in combination with a standardized mixture of internal standards on a nanofluidic PCR platform (e.g., a high density array). In yet another embodiment, the kit further comprises a pair of primers capable of binding to and amplifying a reference sequence. In yet other embodiments, the kit comprises a sterile container which contains the primers; such containers can be boxes, ampules, bottles, vials, tubes, bags, pouches, blister-packs, or other suitable container form known in the art. Such containers can be made of plastic, glass, laminated paper, metal foil, or other materials suitable for holding nucleic acids.

The instructions will generally include information about the use of the compositions of the invention in detecting a gene expression profile. In particular embodiments, the gene expression profile diagnoses or characterizes a neoplasia. Preferably, the kit further comprises any one or more of the reagents useful for an analytical method described herein (e.g., standardized reverse transcriptase PCR). In other embodiments, the instructions include at least one of the following: descriptions of the primer; methods for using the enclosed materials for the diagnosis of a neoplasia; precautions; warnings; indications; clinical or research studies; and/or references. The instructions may be printed directly on the container (when present), or as a label applied to the container, or as a separate sheet, pamphlet, card, or folder supplied in or with the container.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

It should be appreciated that the invention should not be construed to be limited to the examples that are now described; rather, the invention should be construed to include any and all applications provided herein and all equivalent variations within the skill of the ordinary artisan.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Figure 1B:
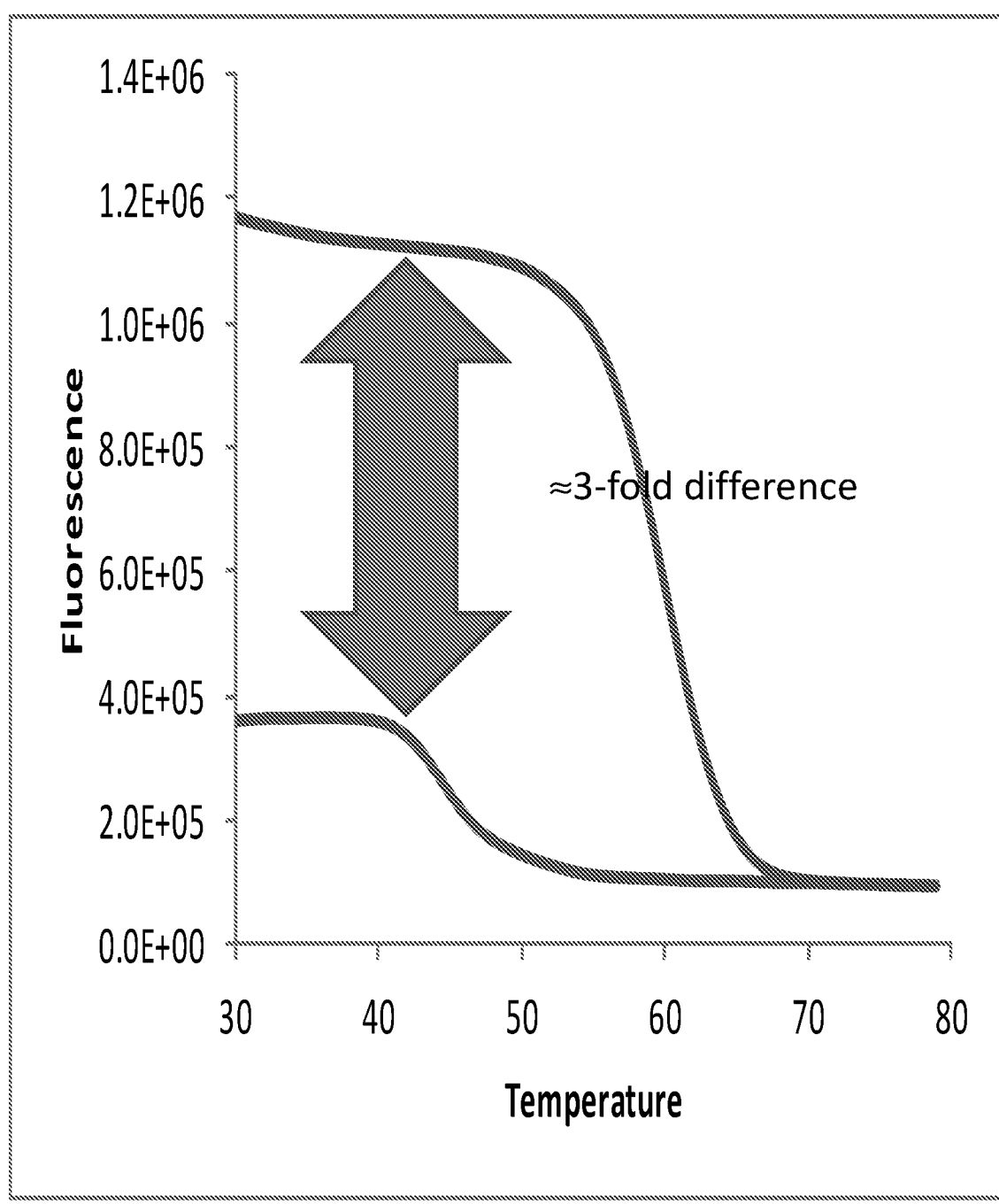

Example 1. Probe Sequences have the Potential to Generate Inaccurate Standardized Nucleic Acid Quantification (SNAQ) Measurements Serial dilutions of IS amplicon were mixed with a fixed quantity of NT, amplified by PCR and measured by melting curve analysis. A source of inaccuracy was discovered unrelated to a difference in IS and NT fluorescent yield. Fraction NT (y-axis) measurements (closed circles) were graphed relative to the input IS:NT ratio (x-axis) (FIG. 1A). The EC50 of this curve was not at 0.0 as expected, but 1.66 (45-fold IS:NT). A graph of IS and NT melting curves that suggested a possible source of error to be a 3-fold fluorescent yield difference between IS and NT melting curves (i.e., given equal molecules of template, IS generates lower fluorescent signal than NT) (FIG. 1B). Thus, the IS signal was scaled 3-fold in an attempt to yield the expected EC50 of 0.0. The scaled melting curve data was closer to the expected curve having an EC50 of 0.0, but did not entirely account for the observed EC50 shift (open circles) (FIG. 1A).

Figure 2A:
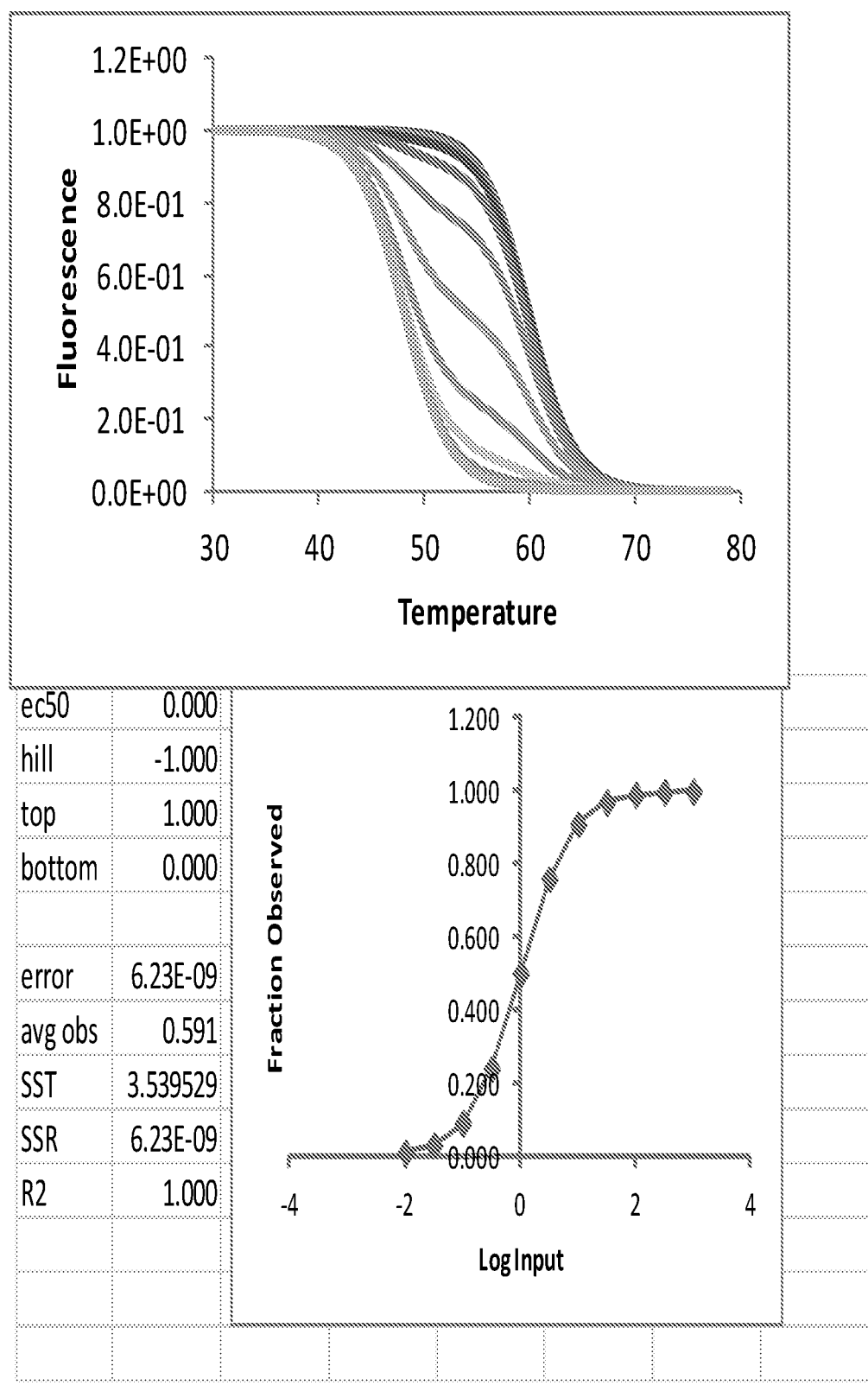
FIGS. 2A and 2B depict modeling of melting curve analysis and fluorescent efficiency. Plots were generated by simulating the melting curves of serially diluted IS relative to a fixed NT quantity. For each dilution simulation, the individual IS and NT curves were simulated using a sigmoid curve with a unique Tm and hill coefficient, and then combined to generate a composite melting curve.
Figure 2B:
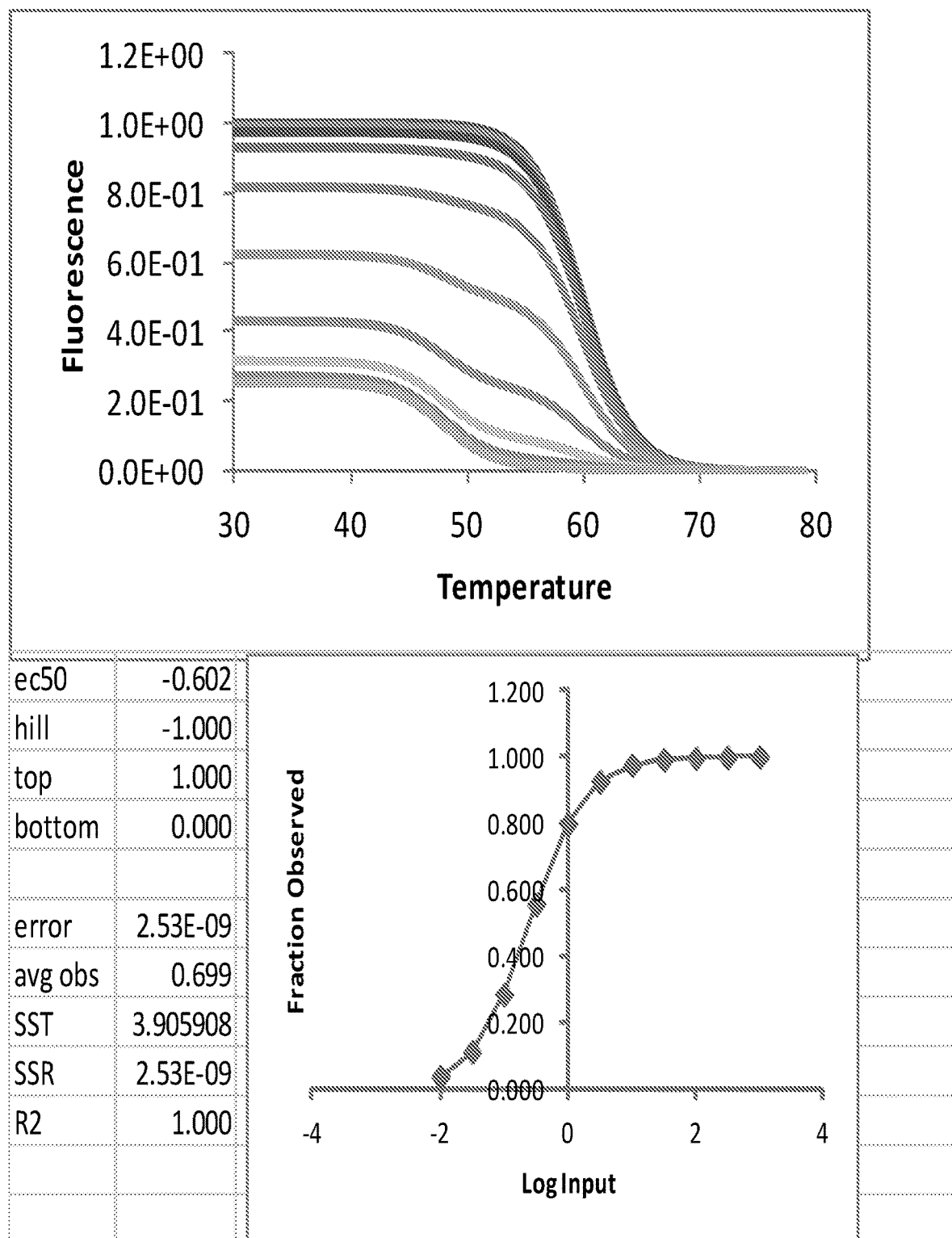

SNAQ measures IS:NT molar ratios using the relative fluorescent signals of each product by melting curve analysis. Models of melting curve analysis and fluorescent efficiency were generated (FIGS. 2A and 2B). Plots were created by simulating the melting curves of serially diluted IS relative to a fixed NT quantity (i.e., a simulation of the data in FIG. 1A). For each dilution simulation, the individual IS and NT curves were simulated using a sigmoid curve with a unique Tm and hill coefficient, and then combined to generate a composite melting curve. Simulated melting curves in which the fluorescence signal of IS alone and NT alone are equal (equal fluorescent efficiency) yielded an EC50 of 0.0. However, not all hybridization probe systems have equal fluorescent efficiency, resulting in a shift in EC50 from 0.0. When melting curves were modeled that have a lower IS fluorescent signal relative to that of NT fluorescent signal (a quarter the fluorescent efficiency), the fraction NT calculated using a two-sigmoid curve fit generated a shift in EC50, which would yield an incorrect result without correcting for the difference in fluorescence efficiency (FIG. 2B). Thus, a shift in EC50 due to lower probe quantum yield can be corrected by scaling the signal according to the difference in fluorescent efficiency. If the EC50 shift in FIG. 1A were simply due to a lower probe quantum yield, then it should have been corrected by scaling the IS signal.

Figure 3A:
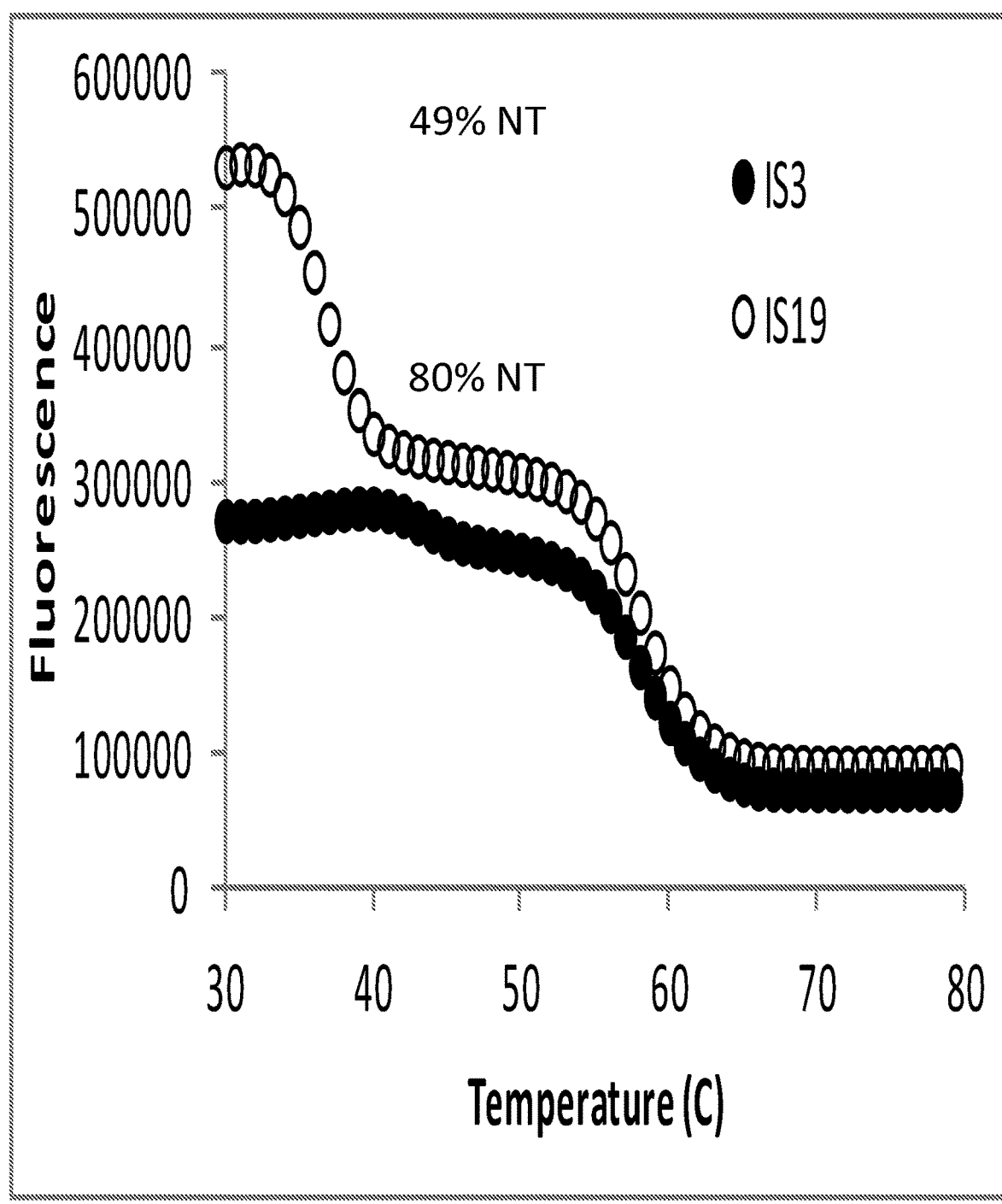
FIGS. 3A and 3B depict melting curve analysis of IS:NT amplicon mixtures. To eliminate the contribution of PCR on the EC50 measurement, NT and an IS PCR amplicon were mixed at different ratios. Additionally, IS templates IS19 and IS20 were designed to eliminate secondary structure from the original IS template IS3.
Figure 3B:
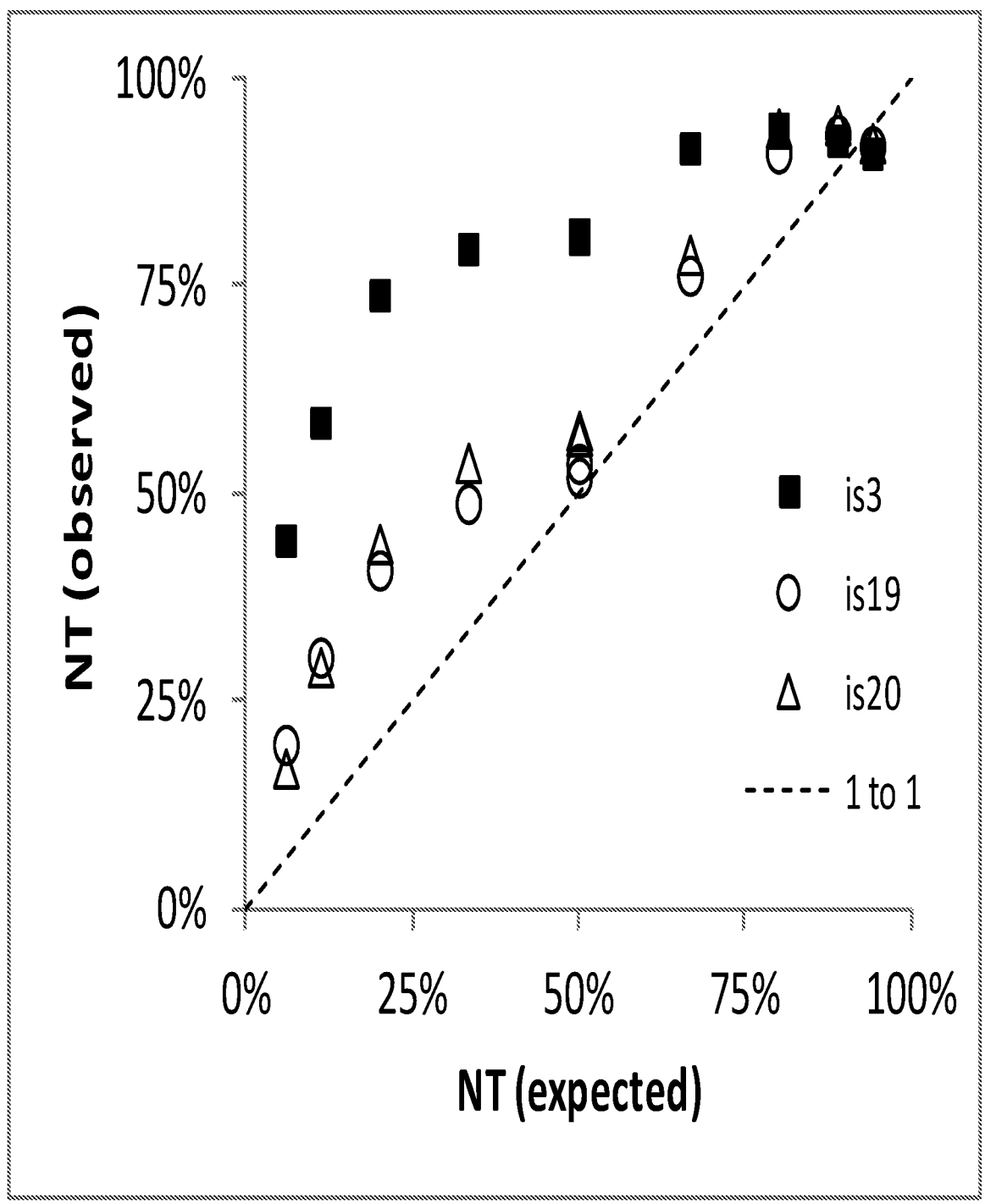

The EC50 shift in FIG. 1A could not be explained by lower probe:IS signal emission. Amplicon was used for IS and NT, which should eliminate the influence of PCR on the outcome. As the templates for NT and IS are competitive, PCR yields should not have been an issue. To eliminate the contribution of PCR on the EC50 measurement, melting curve analysis was performed on mixtures of NT and IS PCR amplicon at different ratios. The original IS melting curve (IS3) at a 2:1 IS:NT amplicon provided an inaccurate melting curve ratio of 1:4 (FIG. 3A, closed circles). The results over the indicated amplicon ratios using IS3 did not show the expected values for NT[observed]:NT[expected] over the entire range of IS:NT ratios (FIG. 3B; solid squares).

DNA single strand folding analysis of IS3 indicated that a stable stem loop structure was present at 35° C. but absent at 55° C. Without being bound to theory, secondary structure has the potential to inhibit the probe binding to the IS. Thus, redesign of the probe binding site can decrease the influence of IS template secondary structure on probe binding, and improve accuracy of melting curve response to IS:NT mixtures.

Two IS templates (IS19 and IS20) were constructed that altered the base pairs in the IS sequence to eliminate the stable secondary structure while producing the desired 15° C. dTM shift between NT and IS. 1519 and 1520 templates are provided at Table 2.

TABLE 2

IS Template Sequences

| Name | Sequence | SEQ ID NO: |
|---|---|---|
| IS3 | GGTTTCTGAATGTCATCGTCCA CTCtGCCAaTGGATTTAAGCAG AGTTCAAAAGCCCTTCAGCGGC CAGTAGCATCTGACTTTGAGC | 1 |
| IS19 | ggtttctgaatgtcatcgtcca ctTagccactAgatttaagcag agttcaaaagcccttcagcggc cagtagcatctgactttgagc | 2 |
| IS20 | ggtttctgaatgtcatcgtcca cAcagccacAggatttaagcag agttcaaaagcccttcagcggc cagtagcatctgactttgagc | 3 |

The melting curve of IS19 (FIG. 3A; open circles) produced 1:1 IS:NT results, which was closer to the expected 2:1 ratio than that indicated by the melting curve of IS3. Both IS19 and IS20 produced responses closer to the expected value over the entire range of IS:NT ratios (FIG. 3B; open circles (IS19) and open triangles (IS20)). Thus, the results indicated that secondary structure (e.g., stem-loop) in the probe binding site distorted the melting curve response and have the potential to lead to errors in ratio measurements if uncorrected.

Results reported herein were obtained using the following methods and materials unless indicated otherwise.

Melting Curve Analysis

Algorithms used for converting melting curve information into molar ratio measurements are known in the art. Briefly, conversion of melting curve data into transcript abundance begins with establishing melting curve parameters for each NT and IS template. Fluorescent probe (e.g., Pleiades) melting curves of samples with either IS or NT template are fit to a variable sloped sigmoid curve, and the resulting Tm and Hill coefficient saved as input parameters for SNAQ analysis. Next, the melting curves for each sample-assay combination are fit to a two sigmoid curve using the parameter inputs defined above, allowing the $Bottom_{IS}$ and $Bottom_{NT}$ to be adjusted to minimize the residuals. The fraction NT is calculated from the $Bottom_{IS}$ and $Bottom_{NT}$ solutions.

Lastly, the S/N is calculated for each sample based on four sample replicates. Accurate SNAQ measurement requires >10 S/N. Assays failing to meet this criterion likely require changes, which can be generated by mutation selection of the internal standard. Occasionally, as designed, the probe does not generate sufficient on/off signal and is replaced. With the wide latitude in probe placement and design (Epoch uses Major Groove Binders and modified nucleotides to adjust binding Tm) and numerous options for internal standard probe binding site mutation type and placement, assays with >50 S/N can be routinely designed.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for detecting a target nucleic acid molecule in a sample, the method comprising the steps of:
   (a) amplifying the target nucleic acid molecule in the presence of a reference nucleic acid molecule and a detectable nucleic acid probe that is capable of hybridizing to the target nucleic acid molecule and the reference nucleic acid molecule;
   (b) identifying binding of the detectable nucleic acid probe to the target nucleic acid molecule and determining the melting temperature of the detectable nucleic acid probe to the target nucleic acid molecule;
   (c) identifying binding of the detectable nucleic acid probe to the reference nucleic acid molecule and determining the melting temperature of the detectable nucleic acid probe to the reference nucleic acid molecule;
   (d) reducing a difference in yield signal between the melting curves for the target nucleic acid molecule and the reference nucleic acid molecule; and
   (e) determining the quantity of the target nucleic acid molecule in the sample using the half maximal effective concentration of the reference nucleic acid molecule;
   wherein reducing a difference in said yield signal comprises one or more of:
   (i) selecting probe binding sites of the target nucleic acid molecule and the reference nucleic acid molecule that have no differences in secondary structure;
   (ii) selecting the reference nucleic acid molecule as having reduced or no secondary structure in the probe binding site; and
   (iii) scaling the yield signal between said melting curves.

2. The method of claim 1, wherein the probe binding site of the target nucleic acid molecule and the probe binding site of the reference nucleic acid molecule have substantial sequence identity.

3. The method of claim 2, wherein said sequence identity is at least 90%.

4. The method of claim 1, wherein the secondary structure is a stem-loop structure or pseudoknot structure.

5. The method of claim 1, wherein the amplifying is by polymerase chain reaction (PCR), competitive PCR, or real-time PCR.

6. The method of claim 1, wherein the sample is a biological fluid or tissue sample derived from a patient.

7. The method of claim 6, wherein the biological fluid is selected from the group consisting of blood, serum, urine, semen and saliva.

8. The method of claim 1, wherein said target nucleic acid is derived from a bacterium, a virus, a spore, a fungus, a parasite, a prokaryotic cell, or a eukaryotic cell.

9. The method of claim 1, wherein the sample is probed to identify a marker associated with a condition selected from the group consisting of neoplasia, inflammation, pathogen infection, immune response, sepsis, the presence of liver metabolites, and the presence of a genetically modified organism.

10. The method of claim 9, wherein marker identification diagnoses a neoplasia, identifies the tissue of origin of the neoplasia, monitors response of the neoplasia to treatment, or predicts the risk of developing a neoplasia.

11. The method of claim 10, wherein the neoplasia is chronic myelogenous leukemia (CML).

12. The method of claim 11, wherein the target nucleic acid is BCR-ABL.

13. The method of claim 1, wherein the target nucleic acid molecule is derived from a bacterial pathogen selected from the list consisting of *Aerobacter, Aeromonas, Acinetobacter, Actinomyces israelli, Agrobacterium, Bacillus, Bacillus antracis, Bacteroides, Bartonella, Bordetella, Bortella, Borrelia, Brucella, Burkholderia, Calymmatobacterium, Campylobacter, Citrobacter, Clostridium, Clostridium perfringers, Clostridium tetani, Cornyebacterium, Corynebacterium diphtheriae, corynebacterium* sp., *Enterobacter, Enterobacter aerogenes, Enterococcus, Erysipelothrix rhusiopathiae, Escherichia, Francisella, Fusobacterium nucleatum, Gardnerella, Haemophilus, Hafnia, Helicobacter, Klebsiella, Klebsiella pneumoniae, Lactobacillus, Legionella, Leptospira, Listeria, Morganella, Moraxella, Mycobacterium, Neisseria, Pasteurella, Pasteurella multocida, Proteus, Providencia, Pseudomonas, Rickettsia, Salmonella, Serratia, Shigella, Staphylococcus, Stentorophomonas, Streptococcus, Streptobacillus moniliformis, Treponema, Treponema pallidium, Treponema pertenue, Xanthomonas, Vibrio,* and *Yersinia*.

14. The method of claim 13, wherein the bacterial pathogen is antibiotic resistant.

15. The method of claim 1, wherein the target nucleic acid molecule is derived from a virus selected from the list consisting of hepatitis C virus, human immunodeficiency virus, Retrovirus, Picornavirus, polio virus, hepatitis A virus, Enterovirus, human Coxsackie virus, rhinovirus, echovirus, Calcivirus, Togavirus, equine encephalitis virus, rubella virus, Flavivirus, dengue virus, encephalitis virus, yellow fever virus, Coronavirus, Rhabdovirus, vesicular stomatitis virus, rabies virus, Filovirus, ebola virus, Paramyxovirus, parainfluenza virus, mumps virus, measles virus, respiratory syncytial virus, Orthomyxovirus, influenza virus, Hantaan virus, bunga virus, phlebovirus, Nairo virus, Arena virus, hemorrhagic fever virus, reovirus, orbivirus, Rotavirus, Birnavirus, Hepadnavirus, hepatitis B virus, Parvovirus, Papovavirus, papilloma virus, polyoma virus, adenovirus, herpes simplex virus 1, herpes simplex virus 2, varicella zoster virus, cytomegalovirus, herpes virus, variola virus, vaccinia virus, pox virus, African swine fever virus, Norwalk virus, and astrovirus.

* * * * *

SEQUENCE LISTING

```
<160> NUMBER OF SEQ ID NOS: 3

<210> SEQ ID NO 1
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggtttctgaa tgtcatcgtc cactctgcca atggatttaa gcagagttca aaagcccttc      60
agcggccagt agcatctgac tttgagc                                          87

<210> SEQ ID NO 2
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggtttctgaa tgtcatcgtc cacttagcca ctagatttaa gcagagttca aaagcccttc      60
agcggccagt agcatctgac tttgagc                                          87

<210> SEQ ID NO 3
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggtttctgaa tgtcatcgtc cacacagcca caggatttaa gcagagttca aaagcccttc      60
agcggccagt agcatctgac tttgagc                                          87
```